United States Patent
Asou et al.

(12) 
(10) Patent No.: US 6,342,241 B1
(45) Date of Patent: Jan. 29, 2002

(54) MEDICAL COMPOSITION OF HYDROXY ACID-BASED OLIGOMER

(75) Inventors: Yukiko Asou, Chiba; Hosei Shinoda, Kanagawa; Hiroaki Tamatani, Chiba, all of (JP)

(73) Assignee: Mitsui Chemicals, Inc. (JP)

( * ) Notice: Subject to any disclaimer, the term of this patent is extended or adjusted under 35 U.S.C. 154(b) by 0 days.

(21) Appl. No.: 09/488,707

(22) Filed: Jan. 21, 2000

(30) Foreign Application Priority Data

Jan. 28, 1999 (JP) .......................................... 11-020116
Dec. 28, 1999 (JP) .......................................... 11-374313

(51) Int. Cl.⁷ ................................................. A61F 13/00
(52) U.S. Cl. ........................ 424/422; 424/486; 424/487
(58) Field of Search ................................ 424/486, 487, 424/422; 524/560

(56) References Cited

U.S. PATENT DOCUMENTS

| | | | | |
|---|---|---|---|---|
| 5,349,047 A | * | 9/1994 | Hermes et al. | ............. 528/361 |
| 5,368,859 A | * | 11/1994 | Dunn et al. | ................. 424/426 |
| 5,399,353 A | | 3/1995 | Bartnik et al. | |
| 5,620,700 A | * | 4/1997 | Berggren et al. | ........... 424/435 |
| 5,725,881 A | | 3/1998 | Buchholz et al. | |

FOREIGN PATENT DOCUMENTS

| | | |
|---|---|---|
| DE | 19908753 A | 8/2000 |
| EP | 0635272 A1 | 1/1995 |
| EP | 635531 A2 | 1/1995 |
| WO | WO96/21427 | 7/1996 |

OTHER PUBLICATIONS

M.A. Tracy et al, "Effects of PLGA End Groups on Degradation", Proceed. Intern. Symp. Control. Rel. Bioact. Mater., $22^{nd}$., pp. 786–787, XP002149477, 1995.

A. Rothen–Weinfold et al, "Analysis of the Influence of Polymer Characteristics and Core Loading on the In Vivo Release of Somatostatin analogue", European Journal of Pharmaceutical Sciences, vol. 5, No. 6, pp. 303–313, XP002149476, Nov. 1997.

* cited by examiner

*Primary Examiner*—Liliana Di Nola-Baron
(74) *Attorney, Agent, or Firm*—Burns, Doane, Swecker, & Mathis, L.L.P.

(57) ABSTRACT

A medical composition is here disclosed which comprises a hydroxy acid-based oligomer (A) and a drug (B), wherein the hydroxy acid-based oligomer (A) is an oligomer in which the carboxylic acid-terminals are at least partially esterified, and the oligomer (A) has a function of becoming pH 5 to 8 when administered into an organism, and the oligomer (A) shows fluidity at 25° C. This composition sustainedly releases the drug (B) to deliver it into an organism by a syringe or the like, and scarcely gives rise to irritation, inflammation or the like.

10 Claims, No Drawings

MEDICAL COMPOSITION OF HYDROXY ACID-BASED OLIGOMER

BACKGROUND OF THE INVENTION

1. Field of the Invention

The present invention relates to a composition of a hydroxy acid-based oligomer (A) and a drug (B), wherein the oligomer (A) has a lactic acid unit useful as a base material for sustained releasing a drug, and holds a fluidity to enable itself to be injected, further, when the oligomer (A) is supplied into water, it is insoluble and does not show an acidity.

2. Description of the Related Art

Heretofore, there has been present an approach that a biological and absorbable polymer is applied to DDS (drug delivery system). The DDS is a system in which the biological and absorbable polymer is used as a base material and the polymer sustainedly releases a drug in according with a proper manner. As an example of the system, there is a method in which a micro sphere of drug is formed by using the biological and absorbable polymer.

Examples of this biological and absorbable polymer include poly-α-hydroxy acids such as polylactic acid (PLA) and polyglycolic acid (PGA). Japanese Patent Application Laid-Open No. 64824/1987 discloses a method that glycolide (GLD) which is a cyclic dimer of glycolic acid and lactide (LTD) which is a cyclic dimer of lactic acid are subjected to ring-opening polymerization to thereby obtain a low-molecular weight polydispersive lactic acid-glycolic acid copolymer (PLGA) which is useful as the basic material for sustainedly releasing a drug. However, in the DDS utilizing the conventional biological and absorbable polymer, every polymer to be used is solid at ordinary temperature, and hence, there is required a contrivance that micro-spheres are dispersed in a dispersion medium such as pure water and then used for injection.

On the other hand, German-A1-3716302 discloses that the biological and absorbable polymer is not used as the micro-spheres but as an absorbable bone wax for a polyester oligomer comprising glycolic acid or lactic acid and glycerin. Furthermore, U.S. Pat. No. 5725881 discloses a mixture of an amorphous and viscous oligomer based on lactic acid having a number-average molecular weight of less than 600 and a crystalline oligomer or polymer based on lactic acid having a number-average molecular weight of from 600 to 10000, i.e., an absorbable material which is plastically deformable and biologically adaptable.

In the technical field of the DDS, however, a base material has been desired that can be mixed with a drug and then injected directly orally (dentistry) or hypodermically by a syringe or the like and has a function of sustainedly releasing a drug component. If a polymer which is used as the base material is acidic (e.g., pH=less than 5) in an organism (under water-soluble conditions), there is a fear that the base material gives rise to irritation, inflammation or the like in the organism. In view of this point, for example, Japanese Patent Application Laid-Open No. 221871/1993 discloses a polypeptide medicament which comprises a polypeptide stable to an acid and a polymer or a copolymer of lactic acid and glycolic acid and which is pharmaceutically active and stable to the acid.

The problems of these conventional techniques can be summarized as follows.

(i) In the case of a hydroxy acid-based oligomer, if a carboxyl group at its molecular terminal is not esterified, the oligomer shows an acidity less than pH 5 when added to distilled water or physiologic saline. Therefore, when such a hydroxy acid-based oligomer is used as the base material and is mixed with a drug, and is administered into an organism, there is a fear that it shows an acidity in the organism and hence causes irritation, inflammation or the like occurs.

(ii) With regard to the hydroxy acid-based oligomer, if the carboxyl group at its molecular terminal is not esterified, its water-solubility is usually high. Therefore, even when such a hydroxy acid-based oligomer is used as the base material and is mixed with a drug, and is administered into an organism, clearance is too rapid, so that a sustained releasable effect of drug cannot be expected.

(iii) A certain kind of hydroxy acid-based oligomer which has no fluidity cannot pass through a needle of a syringe at room temperature (25° C.), so that it cannot be used as the sustained releasable base material for a physiologically active substance.

SUMMARY OF THE INVENTION

An object of the present invention is to solve the above problems of the conventional techniques, concretely to provide a medical composition having the following advantages.

(i) When the medical composition is administered into an organism (inclusive of an oral cavity), a base material does not show an acidity (e.g., less that pH 5), so that irritation, inflammation or the like scarcely occurs.

(ii) The base material is suitably insoluble, so that clearance can be prolonged and hence the sustained releasable effect of drug can be exerted.

(iii) Since the base material shows fluidity at room temperature (25° C.), the medical composition can be administered into the organism by a syringe or the like.

The present inventors have intensively investigated with the intention of achieving the above object, and as a result, it has been found that when a specified hydroxy acid-based oligomer (A) in which the carboxyl group at a molecular terminal is esterified is used, there can be obtained a medical composition which has fluidity at ordinary temperature, is suitably water-insoluble, does not show an acidity in an organism, and particularly has a good sustained releasability. In consequence, the present invention has been completed.

That is to say, the present invention is directed to a medical composition comprising a hydroxy acid-based oligomer (A) and a drug (B), wherein the hydroxy acid-based oligomer (A) is an oligomer in which the carboxylic acid-terminals are at least partially esterified, and the oligomer (A) has a function of becoming pH 5 to 8 when administered into an organism, and the oligomer (A) shows fluidity at 25° C.

DETAILED DESCRIPTION OF THE PREFERRED EMBODIMENTS

A hydroxy acid-based oligomer (A) for use in the present invention has a function of becoming pH 5 to 8 when administered into an organism. Therefore, when a medical composition of the present invention is administered into the organism (inclusive of an oral cavity), it does not become come acidic (less than pH 5), so that a problem of irritation or inflammation which is caused by a low pH scarcely occurs. Thus, the medical composition including the hydroxy acid-based oligomer (A) is very useful as a sustained releasable medical composition.

In the present invention, judgement as to whether or not the hydroxy acid-based oligomer (A) becomes pH 5 to 8 when administered into the organism can pretendedly be made by adding 10 g of a sample to 100 g of distilled water, and then measuring a pH at 37° C. In addition to such a way using distilled water, the judgement can be made by a pretended technique such as (i) a way which comprises adding 10 g of a sample to 100 g of a 0.9% NaCl solution, and then measuring a pH at 37° C., (ii) a way which comprises adding 10 g of a sample to 100 g of a 0.1 N phosphoric acid (pH 7.3) buffer solution, and then measuring a pH at 37° C., or (iii) a way which comprises adding 10 g of a sample to 100 g of physiologic saline, and then measuring a pH at 37° C.

A preferable embodiment of the hydroxy acid-based oligomer (A) for use in the present invention, is a oligomer having a repeating unit represented by the following chemically structural formula (1) and/or a repeating unit represented by the following chemically structural formula (2) as at least a part of repeating units, —R in the following chemically structural formula (3) and/or —R in the following chemically structural formula (4) as one of at least a part of molecular terminals, and —OH in the following chemically structural formula (5) and/or —OH in the following chemically structural formula (6) as another of at least a part of molecular terminals:

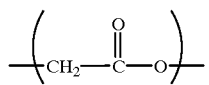

(1)

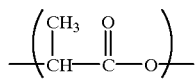

(2)

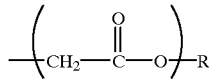

(3)

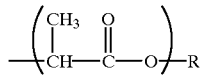

(4)

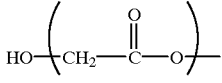

(5)

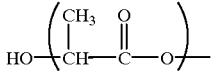

(6)

in the chemically structural formulae (3) and (4), each R is independently an alkyl group having 1 to 4 carbon atoms;

and the oligomer (A) simultaneously satisfies all of the following equations (I) to (V)

$$0 \leq m \tag{I}$$

$$0 \leq n \tag{II}$$

$$2 \leq (n+m) \leq 30 \tag{III}$$

$$0 \leq \left(\frac{m}{n+m}\right) \times 100 \leq 75 \tag{IV}$$

$$25 \leq \left(\frac{n}{n+m}\right) \times 100 \leq 100 \tag{V}$$

wherein m is the number of the repeating unit represented by the above chemically structural formula (1), and n is the number of the repeating unit represented by the above chemically structural formula (2) in one molecule of the oligomer.

In the hydroxy acid-based oligomer (A), 70 mol % or more of the total carboxyl group terminals are preferably esterified with —R in the chemically structural formulae (3) and/or (4), and 70 mol % or more of the other molecular terminals are preferably —OH in the chemically structural formulae (5) and/or (6).

When 10 g of the hydroxy acid-based oligomer (A) for use in the present invention is added to 100 g of distilled water or physiologic saline, preferably 30% by weight or more, more preferably 50% by weight or more, of the oligomer (A) is insoluble at 37° C. Here, no particular restriction is put on a technique for separating an insoluble fraction alone from the hydroxy acid-based oligomer (A), but a technique such as decantation, filtration or centrifugal separation can be utilized. If the amount of insoluble fraction of the hydroxy acid-based oligomer (A) is within the above range, clearance can be suitably prolonged when it is administered into the organism, so that an effect of sustainedly releasing a drug (B) can be increased.

The hydroxy acid-based oligomer (A) for use in the present invention shows fluidity at 25° C. Usually, the oligomer (A) is in a starch syrup state or a gel state, or it is an amorphous polymer.

The fluidity referred to in the present invention can be confirmed as follows: At 25° C., 20 ml of the hydroxy acid-based oligomer is sucked by a 50 ml syringe cylinder (made by Terumo Co., Ltd., disposable type) to which a syringe needle is not set, and then the syringe needle [made by Terumo Co., Ltd., Neolus 21G×1.5 inch (0.80×38 mm)] is set to the syringe cylinder, and afterward, a piston is pushed under an extrusion pressure of 20 kg/cm$^2$ or less by a syringe pump, and at this time, it is observed whether or not the hydroxy acid-based oligomer is completely extruded like a usual injection without any clogging of the syringe needle. In the present invention, the hydroxy acid-based oligomer which can be completely extruded by this procedure (extrusion pressure=20 kg/cm$^2$ or less) is recognized to show the fluidity. In this procedure, it can be considered that the lower the extrusion pressure for the complete extrusion is, the higher the fluidity is. The extrusion pressure for the complete extrusion is preferably 10 kg/cm$^2$ or less, more preferably 5 kg/cm$^2$ or less, most preferably 1 kg/cm$^2$ or less.

The confirmation of the fluidity can also be made by a technique other than the above procedure. For example, a glass plate having length of 500 mm×width of 200 mm set at an angle of 60° to a horizontal surface is spotted at a position 50 mm away from the top end of this glass plate with 1 g of the hydroxy acid-based oligomer, and a time taken for the lower end of the falling oligomer to move as much as 10 mm or more from the spot position is then measured to evaluate the fluidity. This time is preferably 30 minutes or less, more preferably 10 minutes or less, and most preferably 1 minute or less.

In the case that the hydroxy acid-based oligomer (A) for use in the present invention is a copolymer, it is preferably a random copolymer. In comparison with a block copolymer, the random copolymer is excellent in the fluidity.

No particular restriction is put on a preparation method of the hydroxy acid-based oligomer (A). Its typical examples include the following methods (i) to (iv).

(i) A method which comprises heating a lactate such as ethyl lactate, followed by dealcohol condensation.

(ii) A method which comprises reacting a lactide with an alcohol such as ethanol in an amount of 3 to 50 mol % with respect to the total mol of glycolide under substantially water-free conditions to subject the lactide and glycolide to a ring-opening-polymerization. Here, the above substantially water-free conditions mean that the amount of water is 5 mol % or less, preferably 1 mol % or less with respect to the total mol of the lactide and glycolide.

(iii) A method which comprises heating a mixture of a lactate such as ethyl lactate and at least one selected from the group consisting of lactic acid, glycolic acid, lactide, glycolide and glycolate to obtain a copolymer (oligomer).

(iv) A method which comprises mixing two or more kinds of hydroxy acid-based oligomers independently prepared.

In the preparation method of the hydroxy acid-based oligomer (A), a catalyst may be used or may not be used. If the curtailment of a polymerization time is desired, it is preferable to use the catalyst. No particular restriction is put on the kind of catalyst, but for example, tin octanoate, stannous oxide and stannic oxide are preferable. Furthermore, in the above methods (ii) and (iii), the catalyst does not particularly have to be used in the case that the hydroxy acid-based oligomer is obtained by polymerizing the lactide and glycolide.

In the preparation method of the hydroxy acid-based oligomer (A), a reaction temperature is usually in the range of 100 to 200° C., preferably 140 to 180° C., more preferably 150 to 170° C. In the above method (ii), however, it is preferred that the reaction is carried out at a temperature which is decided in consideration of the boiling point of the alcohol to be used, and for example, the reaction may be performed under pressure by the use of an autoclave or the like. In the case that the reaction temperature is higher than the boiling point of the alcohol, it is preferable to use a large amount of the alcohol (e.g., in an amount of 30 to 100 mol % based on the total mol of the lactide and glycolide), because the thus obtained hydroxy acid-based oligomer tends not to show an acidity. In addition, if a meso form lactide is used, the hydroxy acid-based oligomer can be obtained at a temperature lower than the above preferable reaction temperature.

The hydroxy acid-based oligomer (A) for use in the present invention is usually an oligomer containing moieties having different polymerization degrees and a certain molecular weight distribution. Therefore, the numbers m and n of the above repeating units are represented by average values. Furthermore, the weight-average molecular weight of the hydroxy acid-based oligomer (A) is preferably in the range of 200 to 3000 in consideration of fluidity, solubility, viscosity and the like at room temperature (e.g., 25° C.).

The medical composition of the present invention comprises the above hydroxy acid-based oligomer (A) and a drug (B). The amount of the drug (B) is preferably in the range of 0.01 to 100 parts by weight, more preferably 0.01 to 50 parts by weight with respect to 100 parts by weight of the hydroxy acid-based oligomer (A).

No particular restriction is put on the drug (B) for use in the present invention. Typical examples of the drug (B) include medicines and physiologically active substances, and they also include substances, compounds and mixtures which are active to human, animals or plants. That is to say, concrete examples of the drug (B) include not only medicines and physiologically active substances but also agricultural chemicals, cosmetics, fertilizers and the like. In particular, it is very effective to apply the present invention to the drug (B) which is difficult to be absorbed by the human, the animal or the plant and whose activity deteriorates in a short time. Furthermore, it is also very effective to apply the present invention to the drug (B) having a low clearance which is metabolized in an organism to permit the deterioration of its concentration in blood in a short time.

Next, the present invention will be described in more detail in accordance with examples and comparative examples. However, the description of synthetic examples, embodiments, examples and the like in the specification of the present application is for the assistance of the understanding of the contents of the present invention, and it should not be a cause to limit the technical scope of the present invention.

In addition, the weight-average molecular weight (Mw) and the molecular distribution (Mw/Mn) of the hydroxy acid-based oligomer (A) in the examples are values measured by gel permeation chromatography (GPC, solvent= chloroform, standard=polystyrene).

EXAMPLE 1

In a glass reactor equipped with a stirrer, a vacuum line, a nitrogen line and a detachable heater (an oil bath) were placed 236 g (2.0 mol) of ethyl lactate and 21.6 mg of tin octanoate as a catalyst, and the reactor was then immersed in the oil bath (maintained at 160° C.). Afterward, a dry nitrogen gas stream was allowed to flow through the nitrogen line, whereby a reaction system was made with a nitrogen atmosphere, and reaction was then carried out at 160° C. for 24 hours with stirring. Afterward, a part, i.e., about 20 g of the resultant reaction solution was taken out to obtain a liquid oligomer (A1) which was faintly yellow and somewhat viscous. The weight-average molecular weight (Mw) and the molecular weight distribution (Mw/Mn) of this oligomer (A1) were 462 and 2.088, respectively.

Furthermore, 10 g of this oligomer (A1) were thrown into 100 g of distilled water at 37° C., and at this time, the oligomer (A1) was not dissolved and could be recovered as a starch syrup-like insoluble matter in a ratio of 95% by weight. At this time, the pH of an aqueous phase was 6.5.

Moreover, in order to evaluate the fluidity of this oligomer (A1), 20 ml of the oligomer (A1) were sucked by a 50 ml syringe cylinder (made by Terumo Co., Ltd., disposable type) to which a syringe needle was not set, and the syringe needle [made by Terumo Co., Ltd., Neolus 21 G×1.5 inch (0.80×38 mm)] was then set to this syringe cylinder. Afterward, a piston was pushed under an extrusion pressure of 20 kg/cm$^2$ or less by a syringe pump, and at this time, the oligomer (A1) could be completely extruded like a usual injection without any clogging of the syringe needle. That is to say, the oligomer (A1) showed the fluidity at 25° C.

Next, 10 g of the oligomer (A1) were added to 5 g of a 10 wt % acetoaminophenone-methylene chloride solution, followed by stirring, to obtain a uniform solution. This solution was then subjected to reduced pressure, whereby the solvent was recovered, so that a medical composition (drug= acetoaminophenone) of the present invention which was somewhat viscous could be obtained. This medical composition was tested by the use of the same syringe as described above, and as a result, it was apparent that the medical composition was similarly injectable at ordinary temperature (25° C.).

EXAMPLE 2

The reaction solution obtained by the reaction (160° C., 24 hours) in Example 1 was further reacted at 120° C. under 20 mmHg for 10 hours. Afterward, a part, i.e., about 20 g, of the reaction solution was taken out to obtain an oligomer (A2) which was faintly yellow and somewhat viscous. The Mw and the Mw/Mn of this oligomer (A2) were 798 and 1.223, respectively.

Furthermore, 10 g of this oligomer (A2) were thrown into distilled water in the same manner as in Example 1, and at this time, the oligomer (A2) was not dissolved and could be recovered as a starch syrup-like insoluble matter in a ratio of 94% by weight. At this time, the pH of an aqueous phase was 6.8. Moreover, the fluidity of this oligomer (A2) was evaluated in the same manner as in Example 1, and as a result, it was apparent that the oligomer (A2) showed the fluidity at 25° C.

Afterward, the same procedure as in Example 1 was conducted except that this oligomer (A2) was used, thereby obtaining a viscous medical composition of the present invention. This medical composition was also similarly injectable at ordinary temperature (25° C.).

EXAMPLE 3

The reaction solution obtained by the reaction (160° C., 24 hours, and successively 120° C., 20 mmHg, 10 hours) in Example 2 was further reacted at 160° C. under 20 mmHg for 8 hours. Afterward, a part, i.e., about 20 g, of the reaction solution was taken out to obtain an oligomer (A3) which was faintly yellow and viscous. The Mw and the Mw/Mn of this oligomer (A3) were 1356 and 1.2656, respectively.

Furthermore, 10 g of this oligomer (A3) were thrown into distilled water in the same manner as in Example 1, and at this time, the oligomer (A3) was not dissolved and could be recovered as a starch syrup-like insoluble matter in a ratio of 96% by weight. At this time, the pH of an aqueous phase was 6.8. Moreover, the fluidity of this oligomer (A3) was evaluated in the same manner as in Example 1, and as a result, it was apparent that the oligomer (A3) showed the fluidity at 25° C.

Afterward, the same procedure as in Example 1 was conducted except that this oligomer (A3) was used, thereby obtaining a viscous medical composition of the present invention. This medical composition was also similarly injectable at ordinary temperature (25° C.).

EXAMPLES 4 to 10

Each oligomer was synthesized by the same procedure as in Example 1 except that raw materials and a catalyst shown in Table 1 were used, and a medical composition of the present invention was then prepared. A ratio of the catalyst to the total amount of a lactate, lactic acid, glycolic acid, a lactide and glycolide which were the raw materials, was the same as in Example 1. Every composition was injectable at ordinary temperature (25° C.) as in Example 1. The results of evaluations are shown in Table 1. With regard to fluidity, its evaluation in the vicinity of a body temperature (37° C.) is also shown for reference, in addition to the evaluation at ordinary temperature (25° C.). One having the fluidity at each temperature was represented by "○", and one having no fluidity was represented by "x".

COMPARATIVE EXAMPLE 1

In the same glass reactor as used in Example 1 were placed 200 g of lactic acid having a purity of 88%, and this reactor was then immersed in an oil bath (maintained at 160° C.). Afterward, a dry nitrogen gas stream was allowed to flow through a nitrogen line, whereby a reaction system was made a nitrogen atmosphere, and reaction was then carried out at 160° C. under 50 mmHg for 2 hours with stirring. Afterward, a part, i.e., about 20 g of the resultant reaction solution was taken out to obtain an oligomer (A'1) which was transparent and somewhat viscous. The Mw and the Mw/Mn of this oligomer (A'1) were 506 and 3.13, respectively.

Furthermore, 10 g of this oligomer (A'1) were thrown into distilled water in the same manner as in Example 1, and at this time, the oligomer (A'1) was dissolved and its pH was 2.3.

COMPARATIVE EXAMPLE 2

The reaction solution obtained by the reaction (160° C., 50 mmHg, 2 hours) in Comparative Example 1 was further reacted at 160° C. under 20 mmHg for 5 hours. Afterward, a part, i.e., about 20 g, of the reaction solution was taken out to obtain an oligomer (A'2) which was faintly yellow and viscous. The Mw and the Mw/Mn of this oligomer (A'2) were 1250 and 2.99, respectively.

Furthermore, 10 g of this oligomer (A'2) were thrown into distilled water in the same manner as in Example 1, and at this time, the oligomer (A'2) was not dissolved and could be recovered as an insoluble matter in a ratio of 80% by weight. At this time, the pH of an aqueous phase was 2.5.

COMPARATIVE EXAMPLES 3 to 6

Each oligomer was synthesized by the same procedure as in Example 1 except that raw materials and a catalyst shown in Table 1 were used, and it was then evaluated. As a result, it was apparent that the pH of every oligomer was less than 5. Furthermore, the oligomers of Comparative Examples 4 to 6 had no fluidity.

From the results of Examples 1 to 10 shown in Table 1, it is recognized that the medical compositions of the present invention have such effects (i) to (iii) as described hereinafter.

(i) When the medical composition is administered into an organism (inclusive of an oral cavity), it does not show an acidity (e.g., less that pH 5), so that irritation, inflammation or the like scarcely occurs.

(ii) A base material is suitably insoluble, so that when the medical composition is administered into the organism, clearance can be prolonged and hence a sustained releasable effect of drug (B) can be exerted.

(iii) Since the base material shows fluidity at room temperature (25° C.), the medical composition can be administered into the organism as an injection or a drip infusion by a syringe or the like.

The medical composition of the present invention which exerts such effects is very useful in purposes that a drug is injected directly orally (dentistry) or hypodermically by, for example, a syringe or the like to sustainedly release a drug component.

TABLE 1

| | | Raw Material | | | | | Fluidity | |
|---|---|---|---|---|---|---|---|---|
| | L/D | Kind* | Mol Ratio | Catalyst | Mw | Insolubles | pH | 25° C. | 37° C. |
| Example 4 | L | LA-OMe | 1 | Tin Octanoate | 610 | 80 | 6.4 | ○ | ○ |
| Example 5 | L, D | LA-OEt | 1 | Tin Octanoate | 810 | 94 | 6.6 | ○ | ○ |
| Example 6 | L, D | LA-OEt | 1 | Stannic Oxide | 505 | 75 | 6.6 | ○ | ○ |
| Example 7 | L | LTD | 2 | Tin Octanoate | 292 | 80 | 6.7 | ○ | ○ |
| | | EtOH | 1 | | | | | | |
| Example 8 | D | LTD | 4 | None | 438 | 80 | 6.6 | ○ | ○ |
| | L | LA-OEt | 1 | | | | | | |
| Example 9 | L | LA-OEt | 1 | None | 232 | 92 | 6.1 | ○ | ○ |
| | | GLD | 2 | | | | | | |
| Example 10 | | GLD | 1 | None | 262 | 98 | 6.6 | ○ | ○ |
| | L, D | LTD | 1 | | | | | | |
| | | EtOH | 1 | | | | | | |
| Comp. Ex. 3 | L | LA | 1 | None | 290 | 72 | 2.2 | ○ | ○ |
| Comp. Ex. 4 | | GLD | 1 | None | 1200 | 99 | 2.3 | × | × |
| Comp. Ex. 5 | L | LTD | 1 | None | 2500 | 98 | 2.1 | × | × |
| | | GLD | 1 | | | | | | |
| Comp. Ex. 6 | | GA | 1 | Tin Octanoate | 1230 | 99 | 2.3 | × | × |

*LA-OMe = Methyl lactate, LA-OEt = Ethyl lactate, LTD = Lactide, GLD = Glycolide, EtOH = Ethanol

What is claimed is:

1. A medical composition comprising a hydroxy acid-based oligomer (A) and a drug (B), wherein the hydroxy acid-based oligomer (A) is an oligomer in which the carboxylic acid-terminals are at least partially esterified, and the oligomer (A) has a function of becoming pH 5 to 8 when administered into an organism, and the oligomer (A) shows fluidity at 25° C.; wherein the hydroxy acid-based oligomer (A) has a repeating unit represented by the following chemical structural formula (1) and/or a repeating unit represented by the following chemical structural formula (2) as at least a part of repeating units, —R in the following chemical structural formula (3) and/or —R in the following chemical structural formula (4) as one of at least a part of molecular terminals, and —OH in the following chemical structural formula (5) and/or —OH in the following chemical structural formula (6) as another of at least a part of molecular terminals:

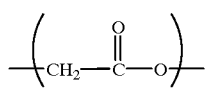 (1)

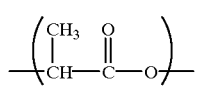 (2)

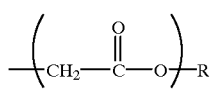 (3)

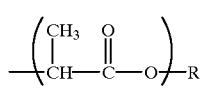 (4)

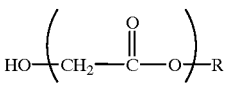 (5)

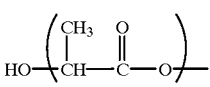 (6)

wherein in the chemical structural formulae (3) and (4), R is ethyl group;
and the oligomer (A) simultaneously satisfies all of the following equations (I) to (V)

$$0 \leq m \quad (I)$$

$$0 \leq n \quad (II)$$

$$2 \leq (n+m) \leq 30 \quad (III)$$

$$25 \leq \left(\frac{n}{n+m}\right) \times 100 \leq 100 \quad (V)$$

wherein m is the number of the repeating units represented by the above chemical structural formula (1), and n is the number of the repeating unit represented by the above chemical structural formula (2) in one molecule of the oligomer.

2. The medical composition according to claim 1 which has a sustained releasability.

3. The medical composition according to claim 1 wherein the hydroxy acid-based oligomer (A) is a random co-oligomer.

4. The medical composition according to claim 1 wherein 30% by weight of the hydroxy acid-based oligomer (A) is insoluble at 37° C. when 10 g of the hydroxy acid-based oligomer (A) is added to 100 g of distilled water.

5. The medical composition according to claim 1 wherein the hydroxy acid-based oligomer (A) is in a starch syrup state at 25° C.

6. The medical composition according to claim 1 wherein the hydroxy acid-based oligomer (A) is in a gel state at 25° C.

7. The medical composition according to claim 1 which contains the drug (B) in an amount of 0.01 to 100 parts by weight with respect to 100 parts by weight of the hydroxy acid-based oligomer (A).

8. The medical composition according to claim 1 wherein the hydroxy acid-based oligomer (A) is an oligomer obtained by heating ethyl lactate to conduct deethanol condensation.

9. The medical composition according to claim 1 wherein the hydroxy acid-based oligomer (A) is an oligomer obtained by reacting a lactide with ethanol in no presence of water or in the presence of water, providing that the amount of the ethanol falls in 3 to 50 mol % with respect to the total mol of the lactide and glycolide, and that the amount of the water, if present, falls in 1 mol % or less with respect to the total mol of the lactide and glycolide.

10. The medical composition according to claim 1 which is used for injection.

* * * * *